United States Patent
Bothe et al.

(10) Patent No.: US 6,977,989 B2
(45) Date of Patent: Dec. 20, 2005

(54) METHOD AND DEVICE FOR X-RAY EXPOSURE CONTROL

(75) Inventors: Uwe Bothe, Prisdorf (DE); Axel Semke, Hamburg (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 99 days.

(21) Appl. No.: 10/326,454

(22) Filed: Dec. 19, 2002

(65) Prior Publication Data

US 2003/0133534 A1 Jul. 17, 2003

(30) Foreign Application Priority Data

Dec. 21, 2001 (DE) ................. 101 63 583

(51) Int. Cl.[7] .............................................. H05G 1/44
(52) U.S. Cl. ..................................... 378/108; 378/116
(58) Field of Search .................... 378/95–97, 108–118, 378/114–116

(56) References Cited

U.S. PATENT DOCUMENTS

| | | | | |
|---|---|---|---|---|
| 3,334,231 A | * | 8/1967 | Bernstein | 378/54 |
| 3,871,579 A | * | 3/1975 | Inamura | 378/108 |
| 4,039,812 A | * | 8/1977 | Grassme et al. | 378/97 |
| 4,097,741 A | * | 6/1978 | Pfeiler et al. | 378/97 |
| 4,158,138 A | * | 6/1979 | Hellstrom | 378/116 |
| 4,454,606 A | * | 6/1984 | Relihan | 378/97 |
| 4,797,905 A | * | 1/1989 | Ochmann et al. | 378/108 |
| 6,222,907 B1 | * | 4/2001 | Gordon et al. | 378/116 |
| 2005/0031082 A1 | * | 2/2005 | Haaga et al. | 378/108 |

FOREIGN PATENT DOCUMENTS

EP    1 035 420 A1    9/2000

* cited by examiner

Primary Examiner—Craig E. Church
Assistant Examiner—Thomas R. Artman
(74) Attorney, Agent, or Firm—Fay, Sharpe, Fagan, Minnich & McKee (57) ABSTRACT

The radiation applied to an object (input dose rate) during irradiation of the object by a radiation source (1) is limited during X-ray exposures. Pairs of values of a control curve which give rise to an input dose rate on the object to be examined which exceeds a predetermined maximum input dose rate are corrected by an arithmetic unit (76). This results in a corrected control curve whose entire length can be used for adjusting the desired tube parameters (tube voltage, tube current or load) without giving rise to the risk of exceeding the maximum input dose rate.

16 Claims, 5 Drawing Sheets

METHOD AND DEVICE FOR X-RAY EXPOSURE CONTROL

BACKGROUND

The invention relates to a method and a device for limiting radiation applied to an object (input dose rate) during irradiation of the object by means of a radiation source, notably during X-ray exposures. The invention also relates to a method and a device for X-ray exposure control while utilizing a method or a device for limiting the input dose rate. The invention also relates to an X-ray generator for carrying out a method of the kind set forth as well as to a corresponding X-ray installation or an X-ray system comprising a device of the kind set forth.

Generally speaking, X-ray installations or systems include one or more X-ray sources, provided with an X-ray tube for generating X-rays, as well as an X-ray generator which is provided with a voltage supply (high-voltage generator) which includes a mains section and delivers the high voltage required for operation of the X-ray tube. When the X-ray source and the components generating the high voltage are combined so as to form one structural unit, such a unit is also referred to as a single-tank generator.

In order to achieve optimum image quality (brightness, contrast, signal-to-noise ratio and sharpness) for the irradiated region, inter alia the intensity of the X-rays incident on the relevant region is of crucial importance. Generally speaking, the image quality is better as the X-ray dose is larger. On the other hand, for obvious reasons it must be ensured that the patient is not exposed to an excessively high dose rate. The maximum value in this respect is imposed by country-specific official rules and regulations.

The dose rate whereto the patient or an object is exposed is dependent essentially on the adjustment of the voltage and the current applied to the X-ray tube, on the distance between the X-ray tube and the object (SSD or Source Skin Distance) as well as on any filters possibly arranged in the beam path between the X-ray tube and the object.

Because these parameters are generally controlled by an automatic exposure device or can be changed by the user during an examination, special steps must be taken so as to ensure that the imposed maximum dose rate whereto the patient is exposed is not exceeded.

EP 1 035 420 discloses a method and a device for exposure control in radiological imaging systems which are intended to solve the problems encountered in respect of the signal-to-noise ratio when the radiation dose on the object is kept constant in the case of a geometrical enlargement of a relevant object due to a change of the distance between an X-ray source and the object or between the X-ray source and an image acquisition device. Therein the input dose is changed in dependence on these two distances in such a manner that a suitable equivalent dose remains constant in the object plane.

SUMMARY

It is a general object of the invention to provide a method and a device whereby an (X-ray) radiation dose rate (input dose rate) applied to an object to be examined can be limited to a selectable maximum value, irrespective of a control curve selected by a user so as to operate the radiation source, as well as irrespective of irradiation conditions such as, for example, the distance between the object and the radiation source, their radiation yield as well as a filter arranged in the beam path.

Furthermore, it is an object of the invention to provide a method and a device for X-ray exposure control in which a selectable maximum input dose rate is not exceeded, irrespective of the control curve and the irradiation conditions, that is, notably when use is made of an automatic exposure device.

It is also an object of the invention to provide a method and a device for X-ray exposure control in which a selectable maximum input dose rate is not exceeded, irrespective of said parameters, and which can be used for fluoroscopy as well as for serial exposures (single images).

Finally, it is also an object of the invention to provide an X-ray generator which includes a device for carrying out one of the above-mentioned methods.

The object is achieved in conformity with a method for limiting radiation applied to an object (input dose rate) during irradiation of the object by means of a radiation source, notably an X-ray source, the radiation source being controlled by way of a control curve (I, II) which is formed by a plurality of pairs of values whereby each time at least one first operating parameter of the radiation source is associated with a second operating parameter of the radiation source, the control curve being corrected in dependence on irradiation conditions in such a manner that the input dose rate is not exceeded for any of the pairs of values during the irradiation.

The object is achieved in conformity with an apparatus by means of a device for carrying out the method, which device includes a first storage device for at least one control curve as well as at least one yield curve, a programmable arithmetic unit for calculating the corrected control curve, as well as a second storage device for storing the corrected control curve.

A special advantage of these solutions resides in the fact that a corrected control curve is available whose entire length can be used for the adjustment of desired tube parameters (tube voltage, tube current or load) and hence for the optimizing of the image quality, without giving rise to the risk of exceeding the maximum input dose rate.

The dependent claims relate to advantageous further embodiments of the invention.

Other claimed embodiments concern preferred control curves whereas additional claims describe preferred irradiation conditions and the way of taking such conditions into account.

The following description, claims and accompanying drawings set forth certain illustrative embodiments applying various principles of the present invention. It is to be appreciated that different embodiments applying principles of the invention may take form in various components, steps and arrangements of components and steps. These described embodiments being indicative of but a few of the various ways in which some or all of the principles of the invention may be employed in a method or apparatus. The drawings are only for the purpose of illustrating an embodiment of an apparatus and method applying principles of the present invention and are not to be construed as limiting the present invention.

DESCRIPTION OF THE DRAWINGS

The foregoing and other features and advantages of the present invention will become apparent to those skilled in the art to which the present invention relates upon consideration of the following detailed description of apparatus applying aspects of the present invention with reference to the accompanying drawings, wherein.

DESCRIPTION

Figure 1:
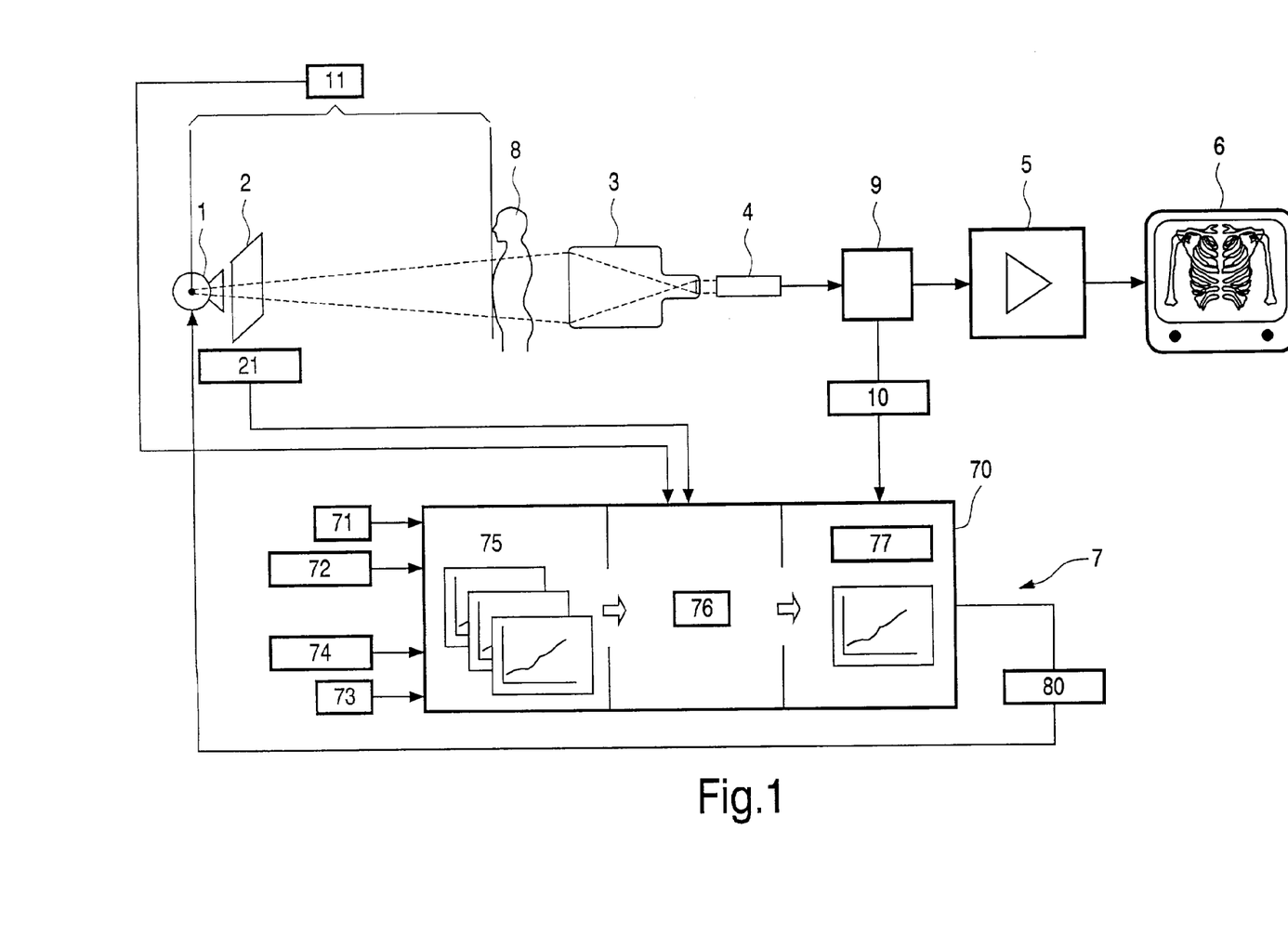
FIG. 1 shows a block diagram of an X-ray system in accordance with the invention.

FIG. 1 shows a block diagram of an X-ray system in accordance with the invention. The system includes an X-ray source in the form of an X-ray tube 1 whereby X-rays are directed onto an object 8 to be examined (a patient). The distance between the focal point of the X-ray tube and the entrance plane of the object to be examined (SSD or Source Skin Distance) is measured by means of a distance measuring device 11. For given examinations a filter 2 may be arranged between the X-ray source 1 and the object 8 to be examined. The type of filter used is detected by means of a filter sensor device 21.

The radiation having traversed the object 8 to be examined is detected by a detector 3, for example, a secondary electron multiplier (image intensifier) so as to be converted into a corresponding image signal by a camera 4. The image signal is subsequently conducted via a beam splitter with a dose rate sensor 9 whereby the dose rate behind the object is measured and a corresponding dose rate signal (10) is generated. The image signal is subsequently processed in a video amplifier 5 after which it is displayed on a monitor 6.

For operation of the X-ray tube 1 there is provided an X-ray generator 7 which consists essentially of a control device 70 and a voltage supply unit 80 for the X-ray tube 1 which is controlled by said control device 70 which may be constructed so as to form part of the X-ray generator or also as a separate unit.

The control device 70 receives the distance signal formed by the distance measuring device 11, the filter signal formed by the filter sensor device 21 and the dose rate signal (10) formed by the dose rate sensor 9.

Furthermore, a user can make various adjustments or selections in respect on the control unit 70. These activities are essentially the selection (71) of the appropriate control curve for the relevant examination, the adjustment (72) of a maximum dose rate on the object to be examined (input dose rate) which may not be exceeded during the examination, the adjustment (73) of the initial values of the tube voltage and/or the tube current on the basis of which an automatic exposure device controls the exposures as well as, in the case of serial exposures (individually exposed static images), the adjustment (74) of a pulse repetition frequency for the tube voltage.

The control device 70 includes essentially a first storage device 75 for a plurality of control curves for the operation of the X-ray tube. The control curves are formed each time by a plurality of pairs of values whereby a first operating parameter of the X-ray tube is associated each time with a second operating parameter of the X-ray tube, for example, the tube voltage with the tube current or a load.

The plurality of control curves implements different control profiles which can be selected by the user of the system as a function of the type of examination so as to achieve an optimum image quality.

The first storage device 75 also serves to store a plurality of yield curves which are formed each time by a plurality of pairs of values whereby the number of first or second operating parameters is associated each time with a dose rate which can be achieved thereby and which is normalized to a tube current as well as to a distance from the X-ray tube.

The control device 70 also includes an arithmetic unit 76 which selects an appropriate yield curve as a function of the type of X-ray tube used as well as of the applied signals (notably the filter signal) and the adjustments made, and which arithmetically corrects the control curve selected by the user, as well as a second storage device 77 for storing the corrected control curve.

The automatic exposure device (not shown) determines, in dependence on the dose rate signal (10) generated by the dose rate sensor 9, the value of the first operating parameter which is appropriate for optimum exposure. The value of the second operating parameter which is associated with this value of the first operating parameter is determined on the basis of the corrected control curve. This pair of values is then applied to the voltage supply unit 80.

Finally, the voltage supply unit 80 is connected to the X-ray tube 1 and generates, in conformity with the pair of values received, the voltages and currents which are necessary for the operation of the X-ray tube 1 and exhibit the appropriate variation in time (for example, square-wave pulse shape) in the case of serial exposures.

In order to carry out an X-ray examination, the X-ray tube 1 and the object 8 to be examined must be moved relative to one another to a position which is optimum for the imaging of the region to be examined.

Because of a relative motion in the direction of the X-ray beam, the dose rate is increased or reduced at the area of entry of the object to be examined. In the case of a relative motion in a direction perpendicular to the X-ray beam, the beam will generally traverse regions of the object to be examined which have different absorption properties. Both directions of movement thus lead to a change of the dose rate on the image intensifier 3 and hence also to a change of the brightness of the image displayed on the monitor 6.

Because a reduction of the dose rate taken up affects the image quality, the voltage and/or the current applied to the X-ray tube 1 is automatically increased in proportion by the automatic exposure device, or possibly also manually, when the dose rate decreases. However, it is then also necessary to take into account the fact that on the one hand an excessive increase of the dose rate may lead to over-exposure of details in the image formed. On the other hand, for reasons of health, of course, it is also necessary to keep the radiation load for the patient as small as possible and a predetermined maximum input dose rate should not be exceeded for the patient.

Care should be taken notably when the distance between the X-ray tube and the patient is changed or when a different filter is inserted in the beam path, because the input dose rate could then be substantially increased.

The control device 70 is conceived in such a manner that the maximum input dose rate is not exceeded anywhere in the control range of the automatic exposure device. This achievement will be described in detail hereinafter on the basis of an example.

Figure 2:
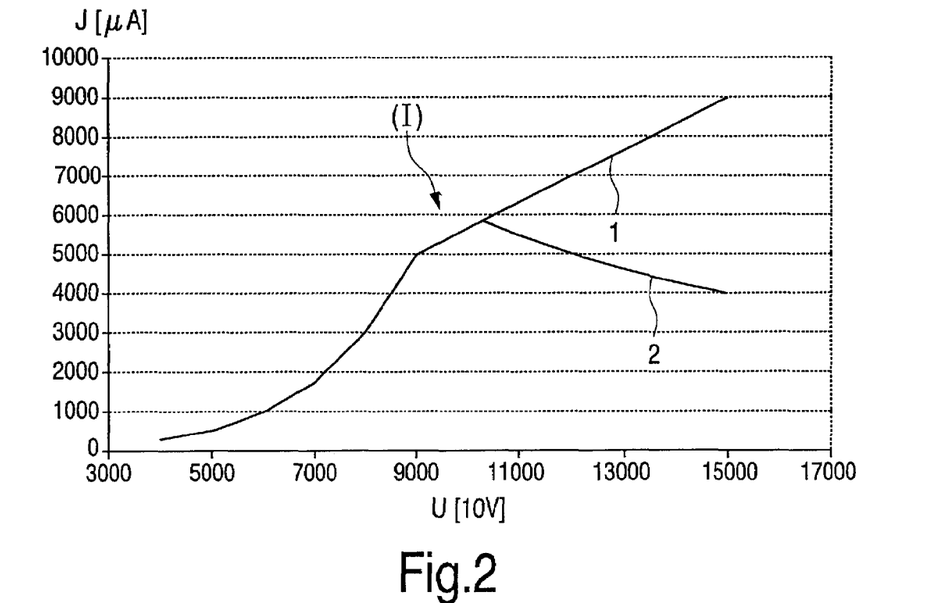
FIG. 2 shows a first control curve of an X-ray tube.
Figure 3:
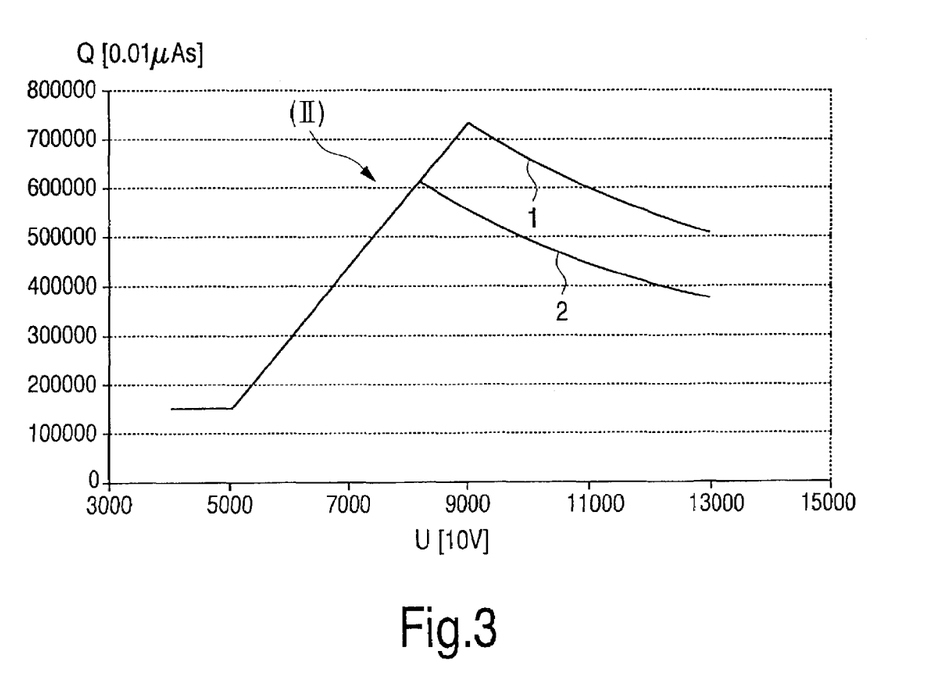
FIG. 3 shows a second control curve of an X-ray tube.

More specifically, as has already been mentioned the control device 70 stores a plurality of first control curves for the fluoroscopy whereby different tube voltages U are associated each time with the corresponding tube currents I. Furthermore, the control device stores a plurality of second control curves for serial exposures whereby the corresponding load values Q are associated with each time different tube voltages U. FIG. 2 shows, by way of example, one of the first control curves (I) whereas FIG. 3 shows one of the second control curves (II).

Figure 4:
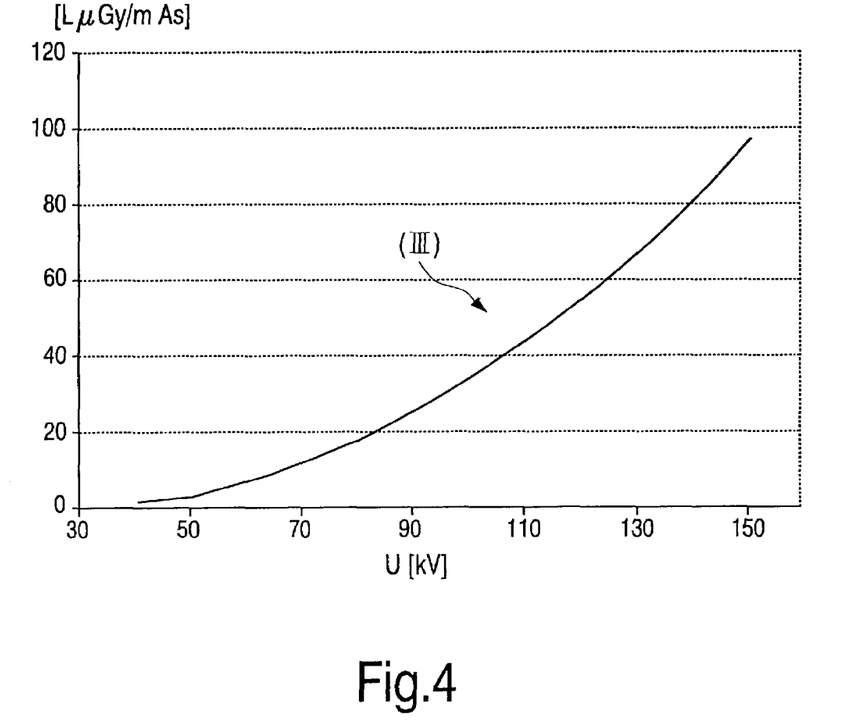
FIG. 4 shows a yield curve of an X-ray tube as a function of a voltage applied thereto.

The yield curves (III) which are also stored and one of which is shown in FIG. 4 describe each time the relationship between the tube voltage U applied to the X-ray tube and the dose rate Y thus obtained per mA of the tube current while taking into account a filter possibly inserted in the beam path, that is, in a distance from the X-ray tube normalized to one meter (yield). Each X-ray exposure is thus based on the yield curve associated with the filter and the X-ray tube used.

In order to ensure that a preset maximum dose rate of the X-rays applied to the object is not exceeded in the case of a change of one or more of the parameters which can be adjusted or selected by the user (notably the distance between the X-ray tube and the object to be examined, the tube voltage, the tube current, the type of tube, the type of filter, the pulse rate), the control curves are corrected while taking into account this maximum input dose rate.

In this respect a distinction should be made between the correction of the first control curves (I) for fluoroscopy and the correction of the second control curves (II) for serial exposures.

For fluoroscopy the first control curve selected by the user is first arithmetically analyzed in order to determine the right upper end of the curve in the rendition of FIG. 2, that is, the value of the highest tube voltage as well as the value of the tube current which is associated with this voltage value. For the example in FIG. 2 a current of 9 mA is obtained for a maximum voltage of 150 kV.

Furthermore, on the basis of the yield curve selected in conformity with the filter (and the X-ray tube) used, the yield for this maximum voltage is determined. For the example shown in FIG. 4 a yield of approximately 96.4 $\mu$Gy/mAs is obtained for a maximum voltage of 150 kV.

The maximum dose rate which would occur at a distance of one meter from the X-ray tube in the case of the maximum tube voltage is obtained by multiplying this yield by the maximum current determined. For said example this maximum dose rate amounts to 867.6 $\mu$Gy/s.

Subsequently, the maximum dose rate which would be incident on the object to be examined is determined by multiplying this value by the inverse square of the actual distance between the X-ray tube and the object to be examined. For a distance of 0.8 m, as determined by means of the distance measuring device 11, a value of 1355.63 $\mu$G/s is obtained for this example.

This value is then compared with the selected value of the maximum input dose rate (for example, 600 $\mu$Gy/s). Division of this maximum value by the calculated value yields a reduction factor (being 0.4426 in the present example) whereby the current value (in this case 9 mA) associated with the highest tube voltage is multiplied. This results in a reduced current value (in this case 3.9834 mA) for the maximum tube voltage and hence a reduced maximum power of 597.51 W.

This pair of values (reduced current value, maximum voltage) is then defined as the upper (last) pair of values in the direction of increasing voltages and hence as the end of the corrected control curve. The variation of the control curve is then corrected on the basis of this upper end in such a manner that the calculated, reduced maximum power, and hence the predetermined maximum input dose rate, is not exceeded in any position.

This is achieved by defining a new (upper) curve segment (2) whereby voltage values below the maximum voltage value are associated each time with respective reduced current values whose product yields each time a power which is equal to or smaller than the reduced maximum power. The new curve segment (2) thus extends in the direction of the original control curve until it intersects this curve, thus replacing the part (1) of the original control curve which is situated above the point of intersection (in this case at 102.5 kV) of these two curves. The corrected control curve is thus composed of a first, lower segment which corresponds to the original variation as well as of the new, second upper segment (2).

The variation of the second upper segment, of course, can be such that, starting from the upper pair of values, the product of the tube voltage and the associated current value is reduced in the direction of the original curve, the point of intersection then being reached only at lower voltage values.

The method is implemented preferably in the form of a program executed by the arithmetic unit 76. The execution of the program will be illustrated on the basis of the flow chart shown in FIG. 5.

Figure 5:
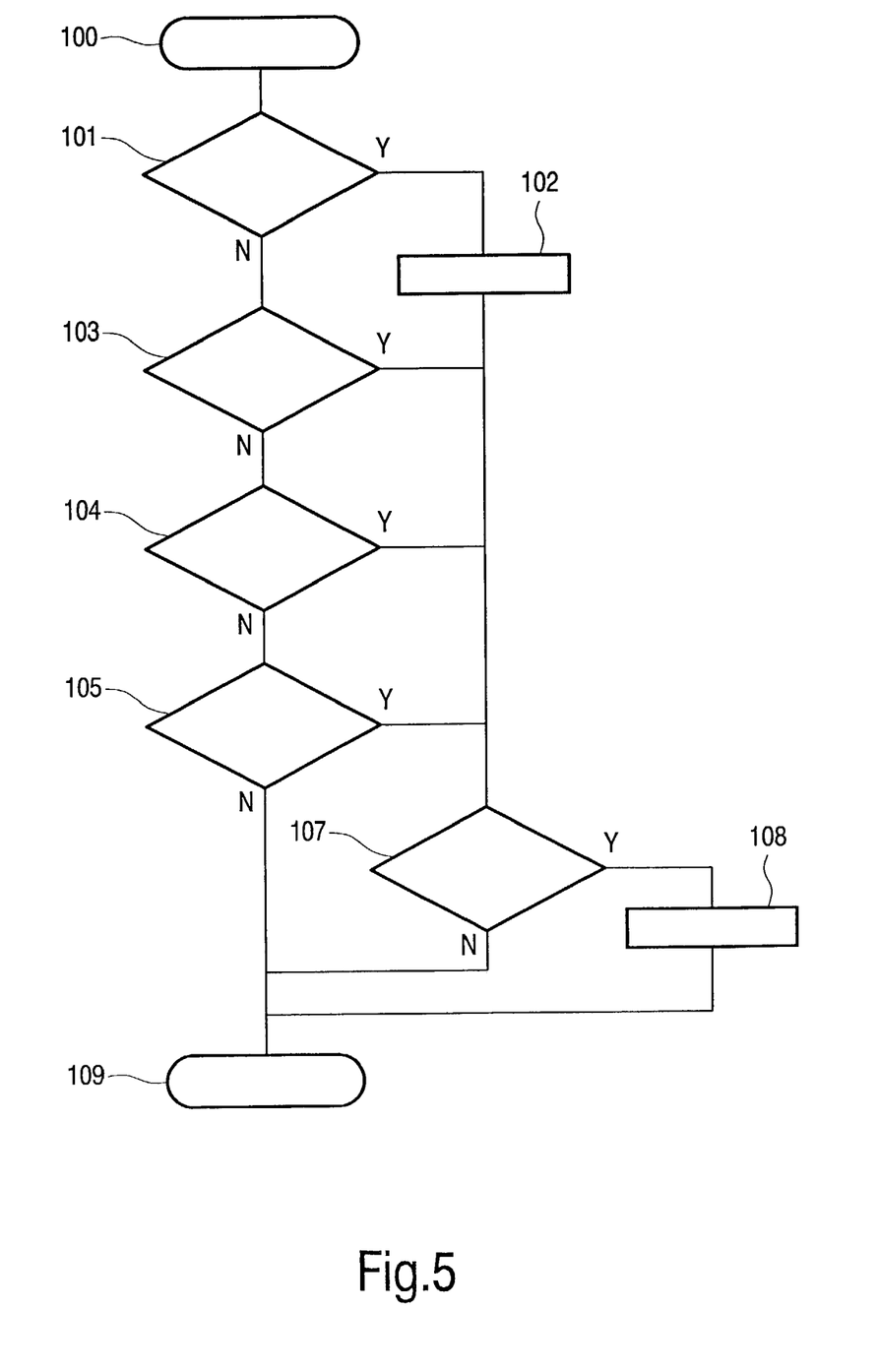
FIG. 5 shows a flow chart of a first method in accordance with the invention.

After the start 100 of the program, it is checked in a first step 101 whether the filter 2 and/or the X-ray tube 1 have been changed after a previously performed curve correction. If this is the case, in a second step 102 the yield curve associated with this new tube/filter combination is selected and the execution is continued in a seventh step 107.

If the result of the check in the first step 101 is negative, in a third step 103 it is checked whether the control curve has been changed since the last correction. If this is the case, the execution continues in the seventh step 107. Otherwise, in a fourth step 104 it is checked whether the distance between the X-ray tube and the object 8 to be examined has changed since the last correction. If this is the case, the execution continues in the seventh step 107; otherwise, in a fifth step 105 it is checked whether the selected maximum input dose rate has been changed since the last correction. If the result of this check is positive, the execution continues in the seventh step 107; otherwise, the method is terminated by way of a ninth step 109.

In the seventh step 107 it is checked whether the first control curve in conformity with FIG. 2 comprises pairs of values whereby the selected maximum input dose rate on the object to be examined can be exceeded. If this is the case, the control curve is corrected in an eighth step 108 so as to be stored in the second storage device 77. The program is then terminated in the ninth step 109, like in the case where the result of the check in the seventh step 107 is negative.

The seventh step 107 and the eighth step 108 are executed, as described above, in the context of the correction of the first control curve.

In order to correct the second control curve (FIG. 3) for serial exposures where the X-ray tube operates in the pulsed mode, the predetermined maximum value of the input dose rate (for example, 800 $\mu$Gy/s) must be divided by the number of exposure intervals per second (that is, the pulse repetition frequency of, for example, 2/s). A maximum dose value is thus obtained for a single pulse (one exposure interval) on which the further illustration is based and which amounts to 400 $\mu$Gy in the present example.

The analysis of the second control curve as selected by the user commences by determining the load obtained for the maximum tube voltage. The curve shown in FIG. 3 yields a load of approximately 5.17 mAs for the maximum voltage of 130 kV.

The yield for the maximum voltage is determined again on the basis of the yield curve selected in conformity with the filter used. For the example shown in FIG. 4 a yield of approximately 67 $\mu$Gy/mAs is obtained for a maximum voltage of 130 kV.

The maximum dose occurring for the maximum tube voltage at a distance of one meter from the X-ray tube is obtained by multiplying said yield by the maximum load determined. This dose amounts to 346.4 $\mu$Gy in said example.

Subsequently, the maximum dose incident on the object to be examined is determined by multiplying this value by the inverse square of the actual distance between the X-ray tube and the object to be examined. In the case of a distance of 0.8 m, as determined by the distance measuring device 11, a value of 541.25 $\mu$Gy is obtained for the present example.

This value is then compared with the previously calculated value of the maximum dose for one pulse (in this case 400 $\mu$Gy). A reduction factor (in this case 0.74) is obtained by dividing this maximum value by the calculated value, the load value calculated by the means of the control curve (in this case being 5.17 mAs) being multiplied by said reduction factor. This results in a reduced load value (in this case being 3.827 mAs) for the maximum tube voltage of 130 kV, and hence in a reduced maximum energy of 495.51 Ws.

This pair of values (reduced load value, maximum voltage) is then defined as the upper (last) pair of values in the direction of increasing voltages and hence as the end of the corrected control curve. The variation of the control curve is then corrected on the basis of this upper end, that is, in such a manner again that the calculated reduced maximum energy, and hence the predetermined maximum input dose rate for the given pulse repetition frequency, is not exceeded in any position.

This is achieved by defining a new (upper) curve segment (2) whereby voltage values below the maximum voltage value are associated each time with reduced load values whose product yields each time an energy which is equal to or smaller than the maximum energy. The new curve segment thus extends in the direction of the original control curve until it intersects this curve, thus replacing the part (1) of the original control curve which is situated above the point of intersection (in this case at 81.2 kV) of these two curves. The corrected control curve is thus composed once more of a first, lower segment which corresponds to the original variation, as well as of the new, second upper segment (2).

The variation of the second upper segment may again be such that, starting from the upper pair of values, the product of the tube voltage and the associated load value is reduced in the direction of the original curve, the point of intersection then being reached only at lower voltage values.

Preferably, this method is again implemented preferably in the form of a program executed by the arithmetic unit 76.

Figure 6:
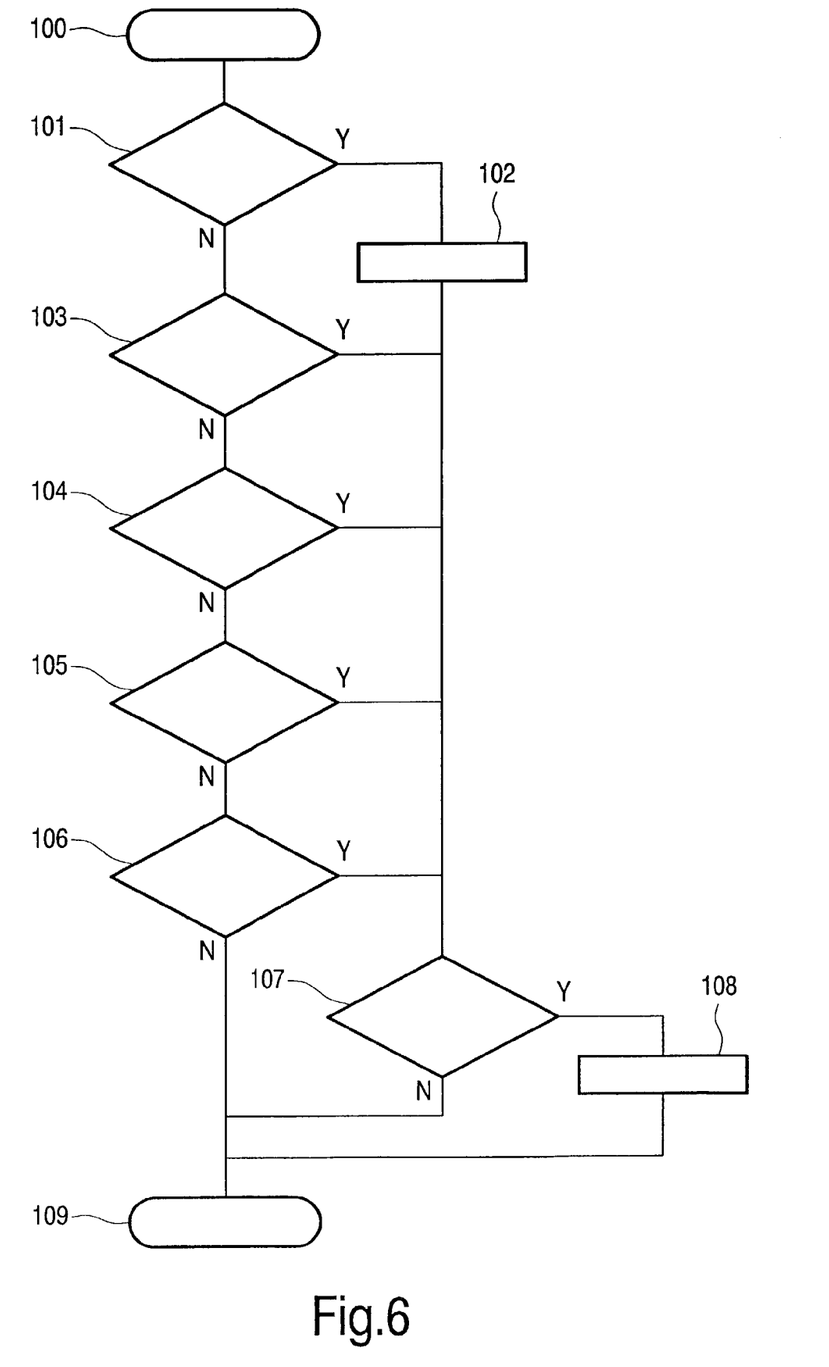
FIG. 6 shows a flow chart of a second method in accordance with the invention.

FIG. 6 shows the essential steps of such a program. This execution of the program is distinct from that shown in FIG. 5 in that after the fifth step 105 there is inserted a sixth step 106 in which it is checked whether the pulse repetition frequency has been changed since the last correction. If this is the case, the execution is continued in the seventh step 107, like in the case of a positive result of the checks in the steps 101 to 105; in the step 107 it is checked whether the second control curve in conformity with FIG. 3 contains pairs of values whereby the selected maximum input dose rate can be exceeded. If the result of this check is positive, the control curve is corrected in the eighth step 108 and the corrected control curve is stored in the second storage device 77.

In conformity with the above description the seventh step 107 and the eighth step 108 are carried out in the context of the correction of the second control curve.

The control curves can also be corrected in such a manner that no new second upper curve segment (2) is determined, but use is made exclusively of the first lower segment; this means that the corrected control curve varies in conformity with the original control curve only as far as the point at which the pair of values is situated whereby the maximum predetermined input dose rate is obtained. One of the special advantages of the invention, however, resides in the fact that this is not necessary, that is, except for a few exceptions.

Other control curves can be used as alternatives for the curves shown in the FIGS. 2 and 3.

One alternative is formed, for example, by control curves for which the first and second operating parameters, plotted on the x axis and the y axis in the FIGS. 2 and 3, respectively, are interchanged.

For example, it is also possible to change the first operating parameter in the form of a pulse width of the tube voltage or the tube current when the X-ray tube operates in the pulsed mode. The maximum input dose rate then corresponds to a maximum pulse width which may not be exceeded.

A further alternative consists in defining a three-dimensional control curve with three operating parameters, one operating parameter being adjusted and the control curve being corrected by the above calculation of one or both other operating parameters. These parameters may be, for example, a pulse repetition frequency as well as the tube voltage and the tube current.

The principle in conformity with the invention can thus be extended to practically any combination of two or more operating parameters, said parameters being first of all the tube voltage, the tube current, the pulse width of these variables in the pulsed mode and the pulse repetition frequency of these variables. A change of the distance between the X-ray tube and the object to be examined and an exchange of filters having a different radiation absorption would also be feasible in this respect.

Finally, the method in accordance with the invention can also be used for photographic single exposures.

The invention is of course not limited to the described or shown embodiments, but generally extends to any embodiment, which falls within the scope of the appended claims as seen in light of the foregoing description and drawings. While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

Having desceibed a preferred embodiment of the invention, the following is claimed:

1. A method for limiting radiation applied to an object during irradiation of the object by means of a radiation source, comprising:
retrieving a control curve for controlling the radiation source corresponding to a selected radiographic procedure, the control curve relating a first operating parameter of the radiation source to a second operating parameter of the radiation source;
retrieving a yield curve corresponding to characteristics of the radiation source, the yield curve relating the first parameter of the radiation source with dose as a function of the second parameter;

for each of a plurality of points along the retrieved control curve, using the yield curve to determine a patient radiation dose rate;

comparing the determined patient dose rate with a preselected maximum dose rate;

altering the retrieved control curve such that the patient dose rate is at or below the preselected maximum dose rate to create a corrected control curve;

using the corrected control curve to control the radiation source during the irradiation of the object such that the maximum dose rate is not exceeded during the irradiation.

2. The method of claim 1 in which the first operating parameter is an X-ray tube voltage and the second operating parameter is an X-ray tube current such that the control curve relates tube voltage to tube current, and the yield curve relates tube voltage to dose rate per unit value of the tube current.

3. The method of claim 1 wherein the first operating parameter is an X-ray tube voltage and the second operating parameter is the product of an X-ray tube current and the exposure time.

4. The method of claim 1 further including:
determining a distance between the object and the radiation source;
adjusting the patient dose in accordance with the measured distance prior to altering the retrieved control curve to create the corrected control curve.

5. The method of claim 1 further including:
determining a type of filter disposed between the radiation source and the object, the yield curve being selected in accordance with the determined filter type.

6. A device for limiting radiation applied to an object during irradiation of the object by means of a radiation source, the device comprising:
a first storage device which stores control curves each corresponding to a selectable radiographic procedure and at least one yield curve characteristic of at least, the radiation source;
a programmable arithmetic unit for calculating a corrected control curve, the programmable arithmetic unit being programmed to perform the steps of:
retrieving a stored control curve and yield curve;
for each of a plurality of points along the retrieved control curve, using the retrieved yield curve to determine a patient radiation dose rate;
comparing the determined patient dose rates with a preselected maximum dose rate;
altering the retrieved control curve such that the patient dose rate is at or below the preselected maximum dose rate to create a corrected control curve;
storing the corrected control curve in a second storage device;
retrieving the corrected control curve from the second storage device;
using the retrieved corrected control curve to control the radiation source during the irradiation of the object such that the maximum dose rate is not exceeded during the irradiation.

7. The device of claim 6 further including:
an X-ray generator;
an automatic exposure control device controlling a voltage supplied to the X-ray generator on the basis of a measured dose rate applied to the object, and on the basis of the corrected control curve.

8. The device of claim 7 wherein the X-ray generator includes:
a voltage supply unit; and
an X-ray tube.

9. The device of claim 8 further comprising:
means for measuring a distance between the X-ray tube and the object, the arithmetic unit further being pro programmed to perform the step of:
adjusting the patient dose in accordance with the measured distance prior to altering the retrieved control curve to create the corrected control curve.

10. A method for limiting radiation applied to an object during irradiation of the object by a radiation source, the method comprising:
before irradiating the object, selecting a control curve for controlling the radiation source, the control curve corresponding to a selected irradiation process, the control curve being formed by a plurality of pairs of values which relate at least one first operating parameter of the radiation source with a second operating parameter of the radiation source;
before irradiating the object, correcting the control curve in dependence on a yield curve which relates dose rate to the first and second operating parameters in such a manner that a preselected maximum dose rate is not exceeded for any of the pairs of values to generate a corrected control curve; and
after generating the corrected control curve, controlling the radiation source during the selected irradiation process with the corrected control curve.

11. The method of claim 10 wherein the first operating parameter is an X-ray tube voltage and the second operating parameter is an X-ray tube current.

12. The method of claim 10 wherein the first operating parameter is an X-ray tube voltage and the second operating parameter is the product of an X-ray tube current and the exposure time.

13. The method of claim 10 wherein the irradiation conditions are defined by at least one of a distance between the object and the radiation source, a radiation yield of the radiation source, and a filter arranged between the radiation source and the object.

14. The method of claim 10 wherein the irradiation conditions are defined in the form of a yield curve formed by a plurality of pairs of values which relate at least one of the operating parameters with a normalized amount of X-rays.

15. An apparatus for limiting radiation applied to an object during irradiation of the object by means of a radiation source, the apparatus comprising:
means for selecting from a storage device a control curve for controlling the radiation source, the control curve formed by a plurality of pairs of values, the control curve relating at least one first operating parameter of the radiation source with a second operating parameter of the radiation source;
a programmable arithmetic unit for calculating a corrected control curve which corrects the selected control curve in dependence on a yield curve which relates dose rate to at least one of a distance between the object and the radiation source, a radiation yield of the radiation source, and a filter disposed between the radiation source and the object in such a manner that a preselected maximum dose rate delivered to the patient is not exceeded for any of the pairs of values along the corrected control curve; and
a means for controlling the irradiation source with the corrected control curve.

16. A device for X-ray exposure control of an X-ray system comprising:

an X-ray source for irradiating an object;

a storage device for storing a plurality of control curves which each relate at least a first operating parameter of the X-ray source to a second parameter of the X-ray source for performing a selected irradiation procedure, at least one yield curve which relates a dose rate to the x-ray source and its operating conditions, and a corrected control curve;

a programmable arithmetic unit for calculating the corrected control curve from the selected control curve and the yield curve such that a dose rate of the corrected control curve does not exceed a preselected maximum dose rate; and an automatic exposure control device for controlling a voltage supply unit for the X-ray tube in accordance with a measured dose rate applied to the object and the corrected control curve.

* * * * *